(12) United States Patent
Harada

(10) Patent No.: US 8,664,205 B2
(45) Date of Patent: Mar. 4, 2014

(54) OIL-IN-WATER EMULSION LOTION CONTAINING 22-OXA-1α, 25-DIHYDROXYVITAMIN $D_3$ AND METHOD OF TREATMENT OF SKIN DISORDER USING THE SAME

(75) Inventor: Shin-ichi Harada, Kyoto (JP)

(73) Assignee: Maruho Co., Ltd., Osaka (JP)

( * ) Notice: Subject to any disclaimer, the term of this patent is extended or adjusted under 35 U.S.C. 154(b) by 716 days.

(21) Appl. No.: 12/162,787

(22) PCT Filed: Jan. 30, 2007

(86) PCT No.: PCT/JP2007/051502
§ 371 (c)(1),
(2), (4) Date: Jul. 30, 2008

(87) PCT Pub. No.: WO2007/086582
PCT Pub. Date: Aug. 2, 2007

(65) Prior Publication Data
US 2009/0176749 A1  Jul. 9, 2009

(30) Foreign Application Priority Data
Jan. 30, 2006  (JP) .................................. 2006-20293

(51) Int. Cl.
*A61K 31/593* (2006.01)
*A61P 17/06* (2006.01)

(52) U.S. Cl.
USPC ......................................................... 514/167

(58) Field of Classification Search
USPC ......................................................... 514/167
See application file for complete search history.

(56) References Cited

U.S. PATENT DOCUMENTS 6,372,233 B1 * 4/2002 Miyauchi et al. ............. 424/401
6,432,422 B1 * 8/2002 Yasukawa et al. ............ 424/401
6,479,058 B1 * 11/2002 McCadden .................... 424/401

FOREIGN PATENT DOCUMENTS

| WO | 98/56388 A1 | 12/1998 |
| WO | 99/29325 A1 | 6/1999 |
| WO | 99/29326 A1 | 6/1999 |
| WO | 99/44617 A1 | 9/1999 |
| WO | 02/17932 A1 | 3/2002 |

* cited by examiner

*Primary Examiner* — San-Ming Hui
*Assistant Examiner* — Kathrien Cruz
(74) *Attorney, Agent, or Firm* — Browdy and Neimark, PLLC

(57) ABSTRACT

Provided is a lotion that exhibits high percutaneous absorption inherent in maxacalcitol, allows the maxacalcitol to be stable, and exhibits less dripping when it is applied to heads. A basic oil-in-water emulsion lotion containing 22-oxa-1α, 25-dihydroxyvitamin $D_3$, medium-chain triglyceride, a nonionic surfactant, and a water-soluble thickener and a method of treatment of skin disorders using the same.

11 Claims, No Drawings

OIL-IN-WATER EMULSION LOTION CONTAINING 22-OXA-1α, 25-DIHYDROXYVITAMIN D$_3$ AND METHOD OF TREATMENT OF SKIN DISORDER USING THE SAME

TECHNICAL FIELD

The present invention relates to an oil-in-water emulsion lotion containing 22-oxa-1α,25-dihydroxyvitamin D$_3$ (hereinafter referred to as maxacalcitol or OCT), which is useful as a skin external preparation and a method of treatment of a skin disorder involving topical application thereof. In particular, the present invention relates to an oil-in-water emulsion lotion which exhibits high percutaneous absorption of maxacalcitol and less skin irritation even if the lotion is made basic in order to improve the chemical stability of maxacalcitol, and a method of treatment of a skin disorder involving topical application thereof.

BACKGROUND ART

Maxacalcitol, which has antiproliferative activity and differentiation activity to skin epidermal cells, has been widely used as an antipsoriatic agent and has received a high evaluation from medical experts in Japan.

Since maxacalcitol is chemically unstable and is readily decomposed in aqueous solutions, it has been believed that an oil-based ointment is a dosage form that can ensure chemical stability of maxacalcitol. Such a dosage form also exhibit high percutaneous absorption, and can be readily applied to trunks of bodies.

However, when an oil-based ointment containing maxacalcitol is applied to hairy areas of psoriasis, which disorder readily appears in not only trunks of bodies but also hairy areas such as heads, the ointment adheres to hair on the hairy areas. This causes a disadvantage in that a sufficient amount of maxacalcitol cannot be applied to affected sites of skin. Therefore, it is highly desired to provide a dosage form of maxacalcitol that can be readily applied to skin in the hairy area. A candidate of such a dosage form is lotion. However, a problem associated with using a lotion containing maxacalcitol is that a lotion generally exhibits percutaneous absorption inferior to that of ointment, and contains purified water which is responsible for the chemical unstableness of maxacalcitol. Further, although it is general that a solution-type lotion can be readily applied to skin compared with ointment, such a lotion readily gets into someone's eye due to dripping during application to his or her head.

WO99/29325 (Patent Document 1) discloses a solution-type lotion containing maxacalcitol and an ether surfactant. The ingredients of this lotion are adjusted such that maxacalcitol can be present in a chemically stable form, and an improvement in percutaneous absorption is expected for the lotion.

WO99/44617 (Patent Document 2) discloses an oil-in-water emulsion lotion that is free from intrusion into eyes due to dripping and that comprises tacalcitol (1α,24-dihydroxyvitamin D$_3$) as an active ingredient, which is an activated vitamin D$_3$ derivative like maxacalcitol; a solid oil component comprising white petrolatum and 0.2 to 1.00 higher alcohol; a liquid oil component comprising squalane; an aqueous phase component comprising ionic polysaccharide; and a nonionic surfactant having a HLB of 10 or above. Since tacalcitol was stable for a long time period in this oil-in-water emulsion lotion, it was anticipated that use of maxacalcitol as an active ingredient instead of tacalcitol was able to form a lotion chemically stable for a long time period. Experiments using maxacalcitol, however, do not show anticipated chemical stability. Furthermore, the percutaneous absorption of maxacalcitol was still unsatisfactory.

With respect to the chemical stability of maxacalcitol in an aqueous injectable solution, WO02/017932 (Patent Document 3) discloses that maxacalcitol is more chemically stable in the solution at a basic pH of about 8.0 than at a neutral pH. However, since a lotion is often exposed to air, stabilization achieved by such a basicity in the solution is not sufficient, and the basic preparation is significantly irritating to skin (Patent Document 1).

Accordingly, it is desired to provide a lotion that exhibits high percutaneous absorption and chemical stability of maxacalcitol, does not cause skin irritation, and exhibits less dripping from a head when it is applied to the head.
Patent Document 1: WO99/29325
Patent Document 2: WO99/44617
Patent Document 3: WO02/017932

DISCLOSURE OF THE INVENTION

Problems to be Solved by the Invention

An object of the present invention is to provide a lotion that exhibits high percutaneous absorption and chemical stability of maxacalcitol, does not cause skin irritation, and exhibits less dripping from a head when it is applied to the head, and a method of treatment of a skin disorder including topical application thereof.

Means for Solving the Problems

As a result of extensive research of the composition of oil-in-water emulsion lotion containing maxacalcitol, the present inventors have successfully developed a lotion which exhibits high percutaneous absorption and chemical stability of maxacalcitol, and does not cause skin irritation regardless of its basicity, while retaining an advantage of common oil-in-water emulsion lotions of less dripping, by adding a medium-chain triglyceride and making the lotion basic.

Therefore, the present invention provides a basic oil-in-water emulsion lotion comprising maxacalcitol, a medium-chain triglyceride, a nonionic surfactant, and a water-soluble thickener, and a method of treatment of a skin disorder in mammals, comprising topically administering the lotion in a therapeutically effective amount to a mammal suffering from skin disorder.

In an embodiment of the present invention, the lotion further comprises a water-soluble polyhydric alcohol.

In the present invention, the chemical stability of maxacalcitol contained in the lotion is improved by adding an organic amine to the lotion to make the lotion basic. As a result, no preservant such as paraben which may cause skin irritation is contained in the lotion and, thus, the safety of the lotion is also improved.

Maxacalcitol contained as an active ingredient, which is known compound, can be synthesized by a method disclosed in, for example, JP 61-267550A. The amount of maxacalcitol contained in the lotion according to the present invention is not limited, so long as it is a therapeutically effective amount for treatment of a skin disorder. However, the amount is in the range of generally 1 to 200 μg/g, preferably 2 to 100 μg/g, and more preferably 5 to 50 μg/g, on the basis of the total weight of the lotion.

The oil phase of the lotion of the present invention comprises maxacalcitol, a medium-chain triglyceride, a nonionic surfactant, and an oleaginous base.

The medium-chain triglyceride, which is a solvent of maxacalcitol, is contained in the oil phase of the lotion of the present invention and significantly contributes to an improvement in percutaneous absorption of maxacalcitol. The inventors believe that medium-chain triglyceride allows maxacalcitol to be present in the form of solution in the lotion. Since the percutaneous absorption of maxacalcitol, however, tends to decrease as the amount of medium-chain triglyceride increases, a relatively low amount of medium-chain triglyceride is preferred in order to enhance percutaneous absorption. On the other hand, medium-chain triglyceride contributes to the formation of the oil phases in the lotion of the present invention. At a significantly low amount, the lotion of the present invention cannot be emulsified. With that background, the content of medium-chain triglyceride is in the range of 0.5 to 25 wt %, preferably 1 to 20 wt %, and more preferably 1 to 10 wt %, on the basis of the total weight of the lotion of the present invention. The medium-chain triglyceride referred to in the present invention is primarily composed of triglyceride of a saturated fatty acid represented by formula $CH_3(CH_2)_nCOOH$ (n=4 to 12). Examples of medium-chain triglyceride include ODO® (NisshinOilliO), COCONAD® (Kao Corporation), Sunfat® MCT-6 (Taiyo Kagaku Co., Ltd.), Delios®, Myritol® 318 (Cognis Japan), PANACET® (NOF CORPORATION), Miglyol® 810, Miglyol® 812 (Mitsuba Trading Co., Ltd.), and JPE PANACET® (YUKA SANGYO CO., LTD.).

When maxacalcitol cannot be readily dissolved in such a solvent, it may be dissolved in a dissolution aid and then dissolved in the solvent. Examples of the dissolution aid include lower alcohols, preferably anhydrous ethanol or 2-propanol, and more preferably anhydrous ethanol. Preferably, the dissolution aid is added in a minimum amount that is required for dissolution of maxacalcitol, since it adversely affects stability of emulsion. The amount of the dissolution aid is in the range of 0.001 to 0.1 wt %, and preferably 0.01 to 0.1 wt %, on the basis of the total weight of the lotion of the present invention.

Preferably, the nonionic surfactant has an HLB value in the range of 7 to 15 and preferably 8 to 11. The structure of the nonionic surfactant is not limited and preferred are of ester type. Examples of ester nonionic surfactant having an HLB value of 8 to 11 include polyoxyethylene glycerol monostearates such as polyoxyethylene (5) glycerol monostearate and polyoxyethylene (15) glycerol monostearate, self-emulsifying glycerol monostearate, polyoxyethylene (15) glycol monostearate, polyoxyethylene (20) hydrogenated castor oil, hexaglycerol monomyristate, sorbitan monolaurate, polyoxyethylene (20) sorbitan tristearate, and polyoxyethylene (30) sorbit tetraoleate. Polyoxyethylene (5) glycerol monostearate is preferred. These may be used alone or in combination of two or more.

The amount of nonionic surfactant contained in the lotion affects the percutaneous absorption of maxacalcitol. Generally, the percutaneous absorption increases as the amount of nonionic surfactant decreases. Since a significantly low amount of nonionic surfactant precludes emulsification, the amount is in the range of 0.001 to 5 wt %, preferably 0.01 to 2.5 wt %, and more preferably 0.05 to 1 wt %, on the basis of the total weight of the lotion of the present invention.

Any oleaginous base generally used in skin external preparations or skin cosmetics can be used without limitation. Examples of the oleaginous base include petrolatum, paraffin, white beeswax, gelling hydrocarbon, carnauba wax, ceresin wax, stearic acid, batyl monostearate, behenic acid, and behenyl alcohol. Preferred is batyl monostearate. The amount of oleaginous base is in the range of 0.001 to 5 wt %, preferably 0.01 to 2.5 wt %, and more preferably 0.05 to 0.5 wt %, on the basis of the total weight of the lotion of the present invention.

The aqueous phase of the lotion of the present invention is composed of water, a water-soluble thickener, and a pH adjuster.

The lotion of the present invention is emulsive and contains the water-soluble thickener that imparts an adequate viscosity not causing dripping to the lotion. Examples of the water-soluble thickener include water-soluble polymers, such as carboxyvinyl polymer, hydroxyethyl cellulose, hydroxypropyl cellulose, and hydroxypropylmethyl cellulose. Preferred is carboxyvinyl polymer, which exhibits satisfactory feeling in application. Examples of the carboxyvinyl polymer include AQUPEC® (SUMITOMO SEIKA CHEMICALS CO., LTD.), Carbopol® 980, Carbopol® 981 (BF Goodrich, CBC, Nikko Chemicals Co., Ltd.), Junlon® (Nihonjunyaku Co., Ltd.), and Hybis Wako® (Wako Pure Chemical Industries, Ltd.). A higher amount of water-soluble thickener is effective for prevention of dripping of the lotion, but causes disadvantages of unsatisfactory feeing in use due to stickiness, and low percutaneous absorption of maxacalcitol. Thus, the amount of water-soluble thickener should be determined carefully. The amount of the water-soluble thickener is in the range of 0.05 to 1 wt %, preferably 0.1 to 0.5 wt %, and more preferably 0.1 to 0.3 wt %, on the basis of the total weight of the lotion of the present invention.

The pH adjuster may be an organic amine, and preferably a $C_1$-$C_6$ mono, di, or trialkanolamine. Examples of such an amine include monoethanolamine, diisopropanolamine, and triethanolamine. Diisopropanolamine is preferred.

In the lotion of the present invention, the active ingredient, maxacalcitol, can be stabilized by making the lotion basic. The basicity is in the range of pH 8 to 11, preferably pH 8.5 to 11, and more preferably pH 9 to 10.5. As described above, WO02/017932 (Patent Document 3) discloses that maxacalcitol can be chemically stabilized in aqueous solution by making the solution basic. According to this disclosure, however, maxacalcitol is the most stable in a basic environment at about pH 8.0. Surprisingly in view of the prior art, high chemical stability is achieved at a pH value much higher than about pH 8.0, in the lotion of the present invention. The pH adjuster described above can be used to adjust the pH value of the liquid to such a high value. It is noted that a pH value higher than 11 will cause skin irritation.

In the present invention, maxacalcitol contained in the lotion is regarded as being "stable" when % residue of maxacalcitol in the lotion is at least 90%, preferably at least 95%, and more preferably at least 96% after storing the lotion for 12 weeks at 50° C., or at least 95% and preferably at least 99% after storing for 24 months at 25° C. and 60% RH.

The aqueous phase in the lotion of the present invention may further contain a water-soluble polyhydric alcohol. A water-soluble polyhydric alcohol has at least two hydroxyl groups in its molecule, and is generally used in skin external preparations or skin cosmetics. Any water-soluble polyhydric alcohols can be used without limitation. Examples of water-soluble polyhydric alcohol include glycerol, propylene glycol, diethylene glycol, dipropylene glycol, 1,3-butylene glycol, polyglycerol, polyethylene glycol 300 to 1500, sorbitol, xylitol, and mannite. Propylene glycol and 1,3-butylene glycol are preferred, and 1,3-butylene glycol is more preferred. The percutaneous absorption of maxacalcitol is also affected by the amount of water-soluble polyhydric alcohol contained in the lotion. As the amount increases, the percutaneous absorption improves. However, a significantly high amount causes unsatisfactory feeling in use due to stickiness. Accordingly, the amount is in the range of 5 to 50 wt %, preferably 10 to 30 wt %, and more preferably 15 to 25 wt %, on the basis of the total weight of the lotion of the present invention. These may be used alone or in combination of two or more.

In a preferred embodiment, the lotion of the present invention comprises 2 to 100 μg/g of maxacalcitol, 1 to 20 wt % of medium-chain triglyceride, 0.01 to 2.5 wt % of ester nonionic surfactant having an HLB value of 8 to 11, 0.1 to 0.5 wt % of carboxyvinyl polymer, 10 to 30 wt % of propylene glycol or 1,3-butylene glycol, and diisopropanolamine in an amount necessary to give a pH value of 8.5 to 11, on the basis of the total weight of the lotion of the present invention.

In a more preferred embodiment, the lotion of the present invention comprises 5 to 50 μg/g of maxacalcitol, 1 to 10 wt % of medium-chain triglyceride, 0.05 to 1 wt % of polyoxyethylene (5) glycerol monostearate, 0.1 to 0.3 wt % of carboxyvinyl polymer, 15 to 25 wt % of 1,3-butylene glycol, and diisopropanolamine in an amount necessary to give a pH value of 9 to 10.5, on the basis of the total weight of the lotion of the present invention.

The oil-in-water emulsion lotion of the present invention exhibits a positive preservative effectiveness even if no preservant is added as described above. However, it may contain a preservant such as a paraben, if necessary. The lotion may further contain a surfactant aid, such as L-arginine, L-histidine, sodium cetyl sulfate, or sodium N-acyl-L-glutamate; and a stabilizer, such as DL-a-tocopherol, sodium citrate, or dibutylhydroxytoluene. When a surfactant aid is used, it is preferably added in a trace amount, that is, 0.0001 to 0.1 wt % and preferably 0.001 to 0.1 wt %, on the basis of the total weight of the lotion of the present invention. When a stabilizer is used, it is added in an amount of 0.01 to 0.5 wt %, preferably 0.05 to 0.2 wt %, and more preferably 0.1 to 0.2 wt %, on the basis of the total weight of the lotion of the present invention. Furthermore, a dye, a flavoring agent, a pigment, an ultraviolet absorber, and/or other additives may be added, if necessary.

The oil-in-water emulsion lotion of the present invention refers to that defined by The Japanese Pharmacopoeia Fourteenth Edition.

The method of forming the oil-in-water emulsion lotion of the present invention is not limited. For example, a predetermined amount of maxacalcitol is dissolved in a predetermined amount of dissolution aid such as ethanol. Separately, a predetermined amount of nonionic surfactant is dissolved in a medium-chain triglyceride which is a oleaginous base component. Then, these solutions are mixed. To the resulting solution, a mixture obtained by adding a predetermined amount of polyhydric alcohol, a predetermined amount of water-soluble thickener and an appropriate amount of a pH adjuster to purified water is added. Finally, to the resulting mixture, the oleaginous base component described above is added in an amount necessary to give a final volume of oil-in-water emulsion lotion.

The oil-in-water emulsion lotion of the present invention can be used in treatment of skin disorders, such as psoriases, e.g. psoriasis vulgaris, ichthyosiform erythroderma, and dykeratosis congenita, e.g., palmoplantar keratoderma, and in particular, in treatment of psoriases. The therapeutically effective dosage depends on the extent of disorder. For example, an oil-in-water emulsion lotion containing 1 to 200 μg/g, preferably 2 to 100 μg/g, and more preferably 5 to 50 μg/g of maxacalcitol is administered once every week to ten times every day, preferably once every two days to four times every day.

Subjects of topical application of the oil-in-water emulsion lotion of the present invention are mammals such as human, dog, cat, cattle, horse, and monkey. A preferred subject is human.

Advantages of the Invention

The present invention provides a lotion containing maxacalcitol which is useful as a skin external preparation, since it exhibits a high chemical stability and a high percutaneous absorption of maxacalcitol, and a less dripping.

BEST MODE FOR CARRYING OUT THE INVENTION

The present invention is described in more detail with reference to Examples and Test Examples, but should not be limited thereto.

EXAMPLES

Examples 1 to 5

Polyoxyethylene (5) glycerol monostearate having an HLB of 9.5, batyl monostearate, dibutylhydroxytoluene, and medium-chain triglyceride (Miglyol 810) were weighed to give the proportion shown in Table 1, mixed, and heated to melt. To the melt, a solution of maxacalcitol in anhydrous ethanol was added to prepare an oil phase. Separately, 1,3-butylene glycol, L-arginine, and diisopropanolamine were dissolved in purified water in the proportion shown in Table 1 to prepare aqueous phase 1. Furthermore, carboxyvinyl polymer (Carbopol 981) was dissolved in purified water to prepare aqueous phase 2. To aqueous phase 1 heated to 60° C., the oil phase heated to 80° C. and aqueous phase 2 heated to 60° C. were added in sequence, and the resulting mixture was stirred to yield an oil-in-water emulsion lotion having a pH value shown in Table 1. The pH value was measured without diluting the lotion using a pH meter made by HORIBA, Ltd. The same measuring procedures were employed in the following examples.

Examples 6 to 11

An oil-in-water emulsion lotion was prepared as described in Example 5, except that the ester nonionic surfactant shown in Table 3 was used instead of polyoxyethylene (5) glycerol monostearate used in Example 5.

Comparative Example 1

According to a process disclosed in WO99/44617, an oil-in-water emulsion lotion containing maxacalcitol was prepared to yield the formulation shown in Table 4. Since maxacalcitol was not dissolved in any of base materials, it was preliminarily dissolved in anhydrous ethanol before use.

Example 12 and Comparative Example 2

An oil-in-water emulsion lotion was prepared as described in Example 5, except that the amount of diisopropanolamine shown in Table 1 was changed to that shown in Table 5 so as to change the pH of the product from basic one to substantially neutral one.

Examples 13 to 18

A lotion was prepared as described in Example 4, except that the amount of diisopropanolamine in the lotion was changed to that shown in Table 8.

Comparative Examples 3 to 6

The following commercially available lotion products were used as Comparative Examples 3 to 6:

Bonalfa™ lotion 2 μg/g: a lotion product containing 0.0002% tacalcitol (available from TEIJIN PHARMA LIMITED) (Comparative Example 3);

Rinderon™ VG lotion: a lotion product containing 1.2 mg of betamethasone valerate and 1 mg of gentamicin sulfate (available from Shionogi & Co., Ltd.) (Comparative Example 4);

Lidomex™ Kowa lotion: a lotion product containing 0.3% prednisolone valerate acetate (available from Kowa) (Comparative Example 5); and Dermovate™ Scalp: a lotion product containing 0.05% clobetasol propionate (available from GlaxoSmithKline) (Comparative Example 6).

Test Example 1

Skin Permeation Test

The products of Examples 1 to 5 and Comparative Example 1 were tested for Skin Permeation Test. A plastic frame (4 cm$^2$) was fixed on hair-shaved back of neck of a hairless mouse under anesthesia. After 20 mg of sample was administered transdermally to the interior of the frame, the frame was fixed with an adhesive bandage. One hour later and four hour later, the skin surface at the administered site were wiped with a cotton swab moistened with 70% ethanol under anesthesia. After the mouse was bled to death, the skin at the administered site was sampled. After the sampled skin was homogenized in methanol, the liquid phase was collected. After the liquid phase was evaporated to dryness, ether and water were added. The ether layer was separated, dried, and then dissolved in ethanol to prepare a sample solution. The sample solution was analyzed with a reverse-phase high-performance liquid chromatograph (column; Inertsil ODS-3 (made by GL Science), detection wavelength; 265 nm, mobile phase; 50 mM ammonium acetate aqueous solution:acetonitrile=60:40) to determine the ratio of the amount of maxacalcitol in the skin to the amount contained in the applied dose.

The results are shown in Tables 1 and 4. The item "OCT concentration in skin" indicates the results of the skin permeability test. A larger value represents higher percutaneous absorption. Examples 1 to 5 containing medium-chain triglyceride (Miglyol 810) show high percutaneous absorption of maxacalcitol.

Test Example 2

Maxacalcitol Stability Test 1

The products of Examples 3 to 12 and Comparative Examples 1 to 2 were tested for maxacalcitol stability under accelerated conditions.

After samples were stored in a temperature and humidity controlled chamber set at 40° C. and 75% RH or a temperature controlled chamber set at 50° C., their maxacalcitol contents were determined. In the determination of the maxacalcitol content, a silver nitrate solution, an internal standard solution, and ethanol were added to 1 g of each sample, and the mixture was agitated. After a sodium chloride solution was added, a part of supernatant liquid collected by centrifugal separation was used as a sample solution. This solution was analyzed with a reverse-phase high-performance liquid chromatograph (column; YMC-Pack A-303 (made by YMC), detection wavelength; 265 nm, mobile phase; water:acetonitrile:tetrahydrofuran mixture=7:4:1) to determine the maxacalcitol content in each sample and calculate % residue of maxacalcitol relative to the initial value.

Test Example 3

Maxacalcitol Stability Test 2

The product of Example 4 was tested for maxacalcitol stability under conditions of long-term stability test.

After samples were stored in a temperature and humidity controlled chamber set at 25° C. and 60% RH, their maxacalcitol contents were determined. The maxacalcitol content was determined as described in Test Example 2. The results are shown in Table 2.

The results of % OCT residue of Test Examples 2 and 3 are shown in Tables 1 to 5. These results demonstrate that maxacalcitol in each product of the present invention is stable at a pH over 8.5. Comparative Example 1 shown in Table 4, where a formulation exhibiting a chemical stability when tacalcitol is used is applied to maxacalcitol, exhibits poor chemical stability of maxacalcitol. Table 5 demonstrates that, while the content of maxacalcitol in the oil-in-water emulsion lotion of the present invention decreases at a neutral pH, it is maintained at a basic pH.

Test Example 4

Viscosity and Flowability Test

The lotion products of Example 4 and Comparative Examples 3 to 6 were tested for viscosity and flowability under the following conditions:

Viscosity test: The viscosity was measured with type E viscometer (B8H, rotor: HH-12, measured at 25° C.).

Flowability test 1: On a glass slide tilted by 45° was placed dropwise 0.5 mL of each sample to measure the time until the sample moves by 50 mm.

Flowability test 2: On a vertical plastic plate (300 mm length) for observation was placed dropwise 0.5 mL of each sample to measure the distance of movement of the sample for 30 seconds.

The results are shown in Table 6. These results demonstrate that the lotion of Example 4 has higher viscosity, lower dripping (lower flowability) than the lotion products of Comparative Examples 3 to 6.

Test Example 5

Irritation Test (Rabbit Eye Mucosa Primary Irritation Test)

To eye of a fixed rabbit, 0.1 ml of product of Example 4 was applied. Then, irritation was determined 1, 3, 24, 48, and 72 hours after the application (the eye was not washed). A group of which each eye was washed with lukewarm water for one minute in 30 seconds from administration of the product was also evaluated similarly. The determination of the extent of irritation was made according to criterion described by Draize (Draize, J. H., Appraisal of the safety of chemical in foods, drugs and cosmetics, Association of Food and Drug Officials of the United State, 49-51, 1959) and the results were evaluated according to the classification described by Kay-Calandra (Kay, J. H. and Valandra, J. C., Interpretation of eye irritation tests, J Soc. Cosm, Chem., 281-289, 1962).

The results are shown in Table 7. They show non-irritation for the eye-unwashed group and almost non-irritation for the eye-washed group.

Test Example 6

Preservative Effectiveness Test

The lotions of Example 4 and Examples 13 to 18 were tested for preservative effectiveness according to the item "Preservative Effectiveness" (category IB) in reference information of The Japanese Pharmacopoeia Fourteenth Edition. In detail, *S. aureus* (bacterium) and *A. niger* (fungus) were separately cultivated according to the description of the Pharmacopoeia to prepare inoculum organism solutions. After each inoculum organism solution was homogeneously mixed with each lotion, each sample was stored for two weeks at 30 to 35° C. for *S. aureus* or 20 to 25° C. for *A. niger*. The numbers of bacteria or fungi in the inoculum organism solution and in the product stored for two weeks were determined by a pour agar plate method. The preservative effectiveness is evaluated as being positive when the number of *S. aureus* bacteria is reduced to 1% or less of that of inoculated bacteria or the number of *A. niger* fungi is equal to or less than that of inoculated fungi.

The results of preservative effectiveness tests against *S. aureus* and *A. niger* are shown in Table 8. For all of the lotions tested against *S. aureus* and *A. niger* which have various basic pH values, preservative effectiveness was evaluated as being positive. The results demonstrate that the oil-in-water emulsion lotion of the present invention which is made basic by adding an adequate amount of diisopropanolamine exhibits a positive preservative effectiveness without any irritative preservant such as a paraben.

[Table 1]

TABLE 1

| Ingredients (wt %) | Example 1 | Example 2 | Example 3 | Example 4 | Example 5 |
|---|---|---|---|---|---|
| Maxacalcitol | 0.0025 | 0.0025 | 0.0025 | 0.0025 | 0.0025 |
| Anhydrous ethanol | 0.1 | 0.1 | 0.1 | 0.1 | 0.1 |
| Medium-chain triglyceride | 1 | 1 | 5 | 5 | 10 |
| Polyoxyethylene (5) glycerol monostearate | 0.2 | 1 | 1 | 0.2 | 1 |
| Batyl monostearate | — | — | — | 0.2 | — |
| Diisopropanolamine | 1.16 | 1.16 | 1.16 | 1.16 | 1.16 |
| 1,3-Butylene glycol | 10 | 10 | 10 | 20 | 10 |
| Carboxyvinyl polymer | 0.2 | 0.2 | 0.2 | 0.2 | 0.2 |
| Dibutylhydrotoluene | 0.1 | 0.1 | 0.1 | 0.1 | 0.1 |
| L-Arginine | — | — | — | 0.001 | — |
| Purified water | balance | balance | balance | balance | balance |
| pH | 9.9 | 10.0 | 10.0 | 9.9 | 10.0 |
| OCT Concentration in skin (% of dose) 1 hour | 10.7 ± 0.9 | 7.4 ± 1.4 | 6.6 ± 2.0 | 5.4 ± 1.2 | 5.2 ± 0.7 |
| 4 hours | 18.3 ± 1.5 | 6.6 ± 0.6 | 3.6 ± 0.2 | 10.4 ± 2.9 | 4.8 ± 2.5 |
| % OCT residue (40° C., 75% RH, 12 weeks) | — | — | 96.3 | 99.2 | 97.9 |
| % OCT residue (50° C., 12 weeks) | — | — | 93.1 | 98.4 | 95.2 |

*OCT: maxacalcitol

TABLE 2

| 25° C., 60% RH | 6 months | 9 months | 12 months | 15 months | 18 months | 21 months | 24 months |
|---|---|---|---|---|---|---|---|
| % OCT residue | 100.0% | 99.8% | 99.7% | 100.0% | 99.7% | 99.8% | 100.3% |

[Table 3]

TABLE 3

| | Ester nonionic surfactant | HLB Value | % OCT residue 40° C., 75% RH, 12 weeks | % OCT residue 50° C., 12 weeks |
|---|---|---|---|---|
| Example 6 | Self-emulsifying glycerol monostearate | 10 | 95.7 | 92.9 |
| Example 7 | Polyoxyethylene (10) glycol monostearate | 11 | 97.2 | 94.5 |
| Example 8 | Polyoxyethylene (20) hydrogenated castor oil | 10.5 | 98.6 | 95.9 |
| Example 9 | Hexaglycerol monomyristate | 11 | 96.2 | 92.9 |
| Example 10 | Sorbitan monolaurate | 8.6 | 94.2 | 90.0 |
| Example 11 | Polyoxyethylene (20) sorbitan tristearate | 10.5 | 96.5 | 93.8 |

[Table 4]

TABLE 4

| Ingredient (wt %) | Comparative Example 1 |
|---|---|
| Maxacalcitol | 0.0025 |
| Anhydrous ethanol | trance |
| DL-α-tocopherol | 0.02 |
| Diisopropyl adipate | 0.5 |
| White petrolatum | 3.5 |
| Paraffin | 0.7 |
| Stearyl alcohol | 0.3 |
| Squalane | 1.7 |
| Oleophilic glycerol monostearate | 0.6 |
| polyoxyethylene (60) hydrogenated castor oil | 1 |
| Polyoxyethylene (23) cetyl alcohol | 1 |
| Methyl hydroxybenzoate | 0.1 |
| Propyl hydroxybenzoate | 0.05 |
| Sodium citrate | 0.57 |
| Propylene glycol | 10 |
| Xanthan gum | 0.6 |
| Disodium hydrogen phosphate | quantum sufficiat |
| Potassium dihydrogen phosphate | quantum sufficiat |
| purified water | balance |
| pH | 7.6 |
| OCT Concentration in skin (% of dose) 4 hours | 3.5 |
| % OCT residue (40° C., 75% RH, 4 weeks) | 87.4 |
| % OCT residue (50° C., 4 weeks) | 76.2 |

[Table 5]

TABLE 5

| Ingredient (wt %) | Example 5 | Example 12 | Comparative Example 2 |
|---|---|---|---|
| Diisopropanolamine | 1.16 | 0.33 | 0.16 |
| pH | 10.0 | 8.5 | 6.5 |
| % OCT residue (40° C., 75% RH, 12 weeks) | 97.9 | 97.3 | 87.4 |
| % OCT residue (50° C., 12 weeks) | 95.2 | 94.9 | 74.2 |

[Table 6]

TABLE 6

| | Viscosity (mPs · s) | Time (seconds) | Moving Distance (mm) |
|---|---|---|---|
| Example 4 | 1,085.4 ± 16.8 | 39.16 ± 2.30 | 103 ± 1.73 |
| Comparative Example 3 | 384.6 ± 2.1 | 2.91 ± 0.41 | 164 ± 4.93 |
| Comparative Example 4 | 477.7 ± 9.6 | 12.12 ± 0.85 | 139 ± 2.65 |
| Comparative Example 5 | 358.9 ± 2.0 | 2.92 ± 0.19 | 203 ± 4.36 |
| Comparative Example 6 | 68.4 ± 4.8 | 0.57 ± 0.10 | 300 or above |

[Table 7]

TABLE 7

| Treatment | Number of animals | Score by Draize (Average) | | | | | Classification by Kay & Calandra |
|---|---|---|---|---|---|---|---|
| | | 1 hr later | 3 hr later | 24 hr later | 48 hr later | 72 hr later | |
| Eye unwashed | 6 | 0.0 | 0.0 | 0.0 | 0.0 | 0.0 | Non-irritation |
| Eye washed | 3 | 0.7 | 0.4 | 0.0 | 0.0 | 0.0 | Almost non-irritation |

[Table 8]

TABLE 8

| | Diisopropanolamine (wt %) | pH | Results ($S.\ aureus$) | | | Results ($A.\ niger$) | | |
|---|---|---|---|---|---|---|---|---|
| | | | Number of inoculated bacteria | Number of bacteria 2 weeks later | Preservative Effectiveness | Number of inoculated fungi | Number of fungi 2 weeks later | Preservative Effectiveness |
| Example 4 | 1.16 | 10.0 | $3.9 \times 10^5$ | <10 | Positive | $2.4 \times 10^5$ | <10 | Positive |
| Example 13 | 0.60 | 9.4 | $4.6 \times 10^5$ | <10 | Positive | $2.5 \times 10^5$ | <10 | Positive |
| Example 14 | 0.55 | 9.3 | $4.6 \times 10^5$ | <10 | Positive | $2.4 \times 10^5$ | $2.0 \times 10$ | Positive |
| Example 15 | 0.50 | 9.2 | $4.6 \times 10^5$ | <10 | Positive | $2.4 \times 10^5$ | $1.0 \times 10^2$ | Positive |
| Example 16 | 0.45 | 9.0 | $4.6 \times 10^5$ | <10 | Positive | $2.4 \times 10^5$ | $1.8 \times 10^2$ | Positive |
| Example 17 | 0.40 | 8.8 | $4.6 \times 10^5$ | <10 | Positive | $2.4 \times 10^5$ | $5.3 \times 10^2$ | Positive |
| Example 18 | 0.35 | 8.5 | $4.6 \times 10^5$ | <10 | Positive | $2.4 \times 10^5$ | $4.6 \times 10^2$ | Positive |

The invention claimed is:

1. A basic oil-in-water emulsion lotion, comprising 22-oxa-1α, 25-dihydroxyvitamin $D_3$, medium-chain triglyceride, a nonionic surfactant, and a water-soluble thickener in the absence of a preservative;
  wherein the basicity is in the range of pH 8.5 to 11 and is provided by adding an organic amine which is a $C_1$-$C_6$ mono-, di-, or trialkanol amine.

2. The lotion according to claim 1, wherein the amount of the medium-chain triglyceride is in the range of 0.5 to 25 wt % on the basis of the total weight of the lotion.

3. The lotion according to claim 1, wherein the nonionic surfactant has a HLB value in the range of 8 to 11.

4. The lotion according to claim 1, further comprising a water-soluble polyhydric alcohol.

5. A method for treating a skin disorder selected from the group consisting of psoriasis, ichthyosiform, erythroderma, dyskeratosis congenita and palmoplantar keratoderma in a mammal, comprising topically administering a therapeutically effective amount of the lotion according to claim 1 to a mammal suffering from a skin disorder selected from the group consisting fo psoriasis, ichthyosiform, erythroderma, dyskeratosis congenita and palmoplantar keratoderma.

6. The method according to claim 5, wherein the amount of the medium-chain triglyceride contained in the lotion is in the range of 0.5 to 25 wt % on the basis of the total weight of the lotion.

7. The method according to claim 5, wherein the basicity of the lotion is in the range of pH 8 to 11.

8. The method according to any one of claim 5, wherein the nonionic surfactant contained in the lotion has an HLB value in the range of 8 to 11.

9. The method according to any one of claim 5, wherein the basicity of the lotion is provided by adding an organic amine.

10. The method according to any one of claim 5, wherein the lotion further comprises a water-soluble polyhydric alcohol.

11. The method according to claim 5, wherein the skin disorder is psoriasis.

\* \* \* \* \*